(12) United States Patent  
Chauvin et al.

(10) Patent No.: US 12,260,066 B1  
(45) Date of Patent: Mar. 25, 2025

(54) APPARATUS, SYSTEM AND METHOD FOR PROCESSING IMMUNIZATION DATA TO GENERATE AN EFFICIENT COMPUTER INTERFACE

(71) Applicant: ALLSCRIPTS SOFTWARE, LLC, Chicago, IL (US)

(72) Inventors: George Chauvin, Ferrisburgh, VT (US); Jefferson Wilson, Williston, VT (US); Jeanne Armstrong, Lebanon, IN (US)

(73) Assignee: Allscripts Software, LLC, Chicago, IL (US)

( * ) Notice: Subject to any disclaimer, the term of this patent is extended or adjusted under 35 U.S.C. 154(b) by 0 days.

(21) Appl. No.: 16/203,585

(22) Filed: Nov. 28, 2018

(51) Int. Cl.  
*G06F 3/0482* (2013.01)  
*G16H 20/10* (2018.01)  
*G16H 50/30* (2018.01)

(52) U.S. Cl.  
CPC .......... *G06F 3/0482* (2013.01); *G16H 20/10* (2018.01); *G16H 50/30* (2018.01)

(58) Field of Classification Search  
CPC ....... G06F 3/0482; G16H 20/10; G16H 50/30  
See application file for complete search history.

(56) References Cited

U.S. PATENT DOCUMENTS

| | | | |
|---|---|---|---|
| 10,340,037 B2* | 7/2019 | Douglass | G16H 10/60 |
| 2014/0006913 A1* | 1/2014 | Gopalakrishna | G06F 16/986 |
| | | | 715/200 |
| 2014/0359429 A1* | 12/2014 | Pellegri | G06F 16/9577 |
| | | | 715/235 |
| 2018/0322249 A1* | 11/2018 | Allen | G16H 10/60 |
| 2018/0322251 A1* | 11/2018 | Allen | G16H 15/00 |
| 2019/0172569 A1* | 6/2019 | Green | G16H 50/20 |
| 2019/0198179 A1* | 6/2019 | Dey | G16H 10/60 |

* cited by examiner

*Primary Examiner* — Yongjia Pan  
(74) *Attorney, Agent, or Firm* — Peter Zura; LOZA & LOZA, LLP

(57) ABSTRACT

Technologies and techniques for generating an efficient computer interface for an immunization regimen. A processing apparatus is coupled to a memory storing immunization data itemsets and medical data itemsets, and a data display control module. The processing apparatus is configured to determine a frequency of immunization data and medical data itemsets associated with a rule for an immunization regimen. Proportions of the itemsets for the immunization regimen are calculated, along with a confidence factor that includes an estimate of the probability a rule portion of a rule includes another rule portion. A computer interface is generated via templates that includes immunization regimen that is based on the confidence factor. The immunization regimen data includes expected frequencies of immunization data.

17 Claims, 10 Drawing Sheets

| Immun. Reg. | Imm1 | Imm2 | Imm3 | MD1 | MD2 |
|---|---|---|---|---|---|
| 1 | 1 | 0 | 1 | 0 | |
| 2 | 1 | 1 | 0 | 1 | 1 |
| 3 | 1 | 0 | 1 | 0 | 1 |
| 4 | 1 | 1 | 0 | 1 | 1 |
| 5 | 0 | 1 | 1 | 1 | 0 |
| 6 | 0 | 1 | 1 | 1 | 0 |
| 7 | 0 | 0 | 1 | 0 | 0 |

APPARATUS, SYSTEM AND METHOD FOR PROCESSING IMMUNIZATION DATA TO GENERATE AN EFFICIENT COMPUTER INTERFACE

FIELD OF TECHNOLOGY

The present disclosure is directed to technologies and techniques for processing an immunization computer interface. More specifically, the present disclosure is directed to processing medical data associated with an immunization database, and modifying an interface to provide better computer performance and display features

BACKGROUND

Historically, many patients do not receive important immunizations and other preventive services and advice because they do not know to see their clinical team for these services, they forget to make appointments, or they miss scheduled appointments. By some estimates, the rate of missed appointments can exceed 50 percent. The impact can be significant. Missed appointments contribute to discontinuity of care, reduce care opportunities for other patients, disrupt the patient-provider relationship, and add to health care costs.

Accordingly, technologies have been developed to tackle the inadequate delivery of preventive services by instituting computer-based reminder and recall systems for patients and health care providers. Reminder systems notify patients a few days before their scheduled appointment, while recall systems contact patients who have missed appointments and encourage them to reschedule. The benefits of reminder and recall systems include improved immunization rates, fewer missed appointments (no-shows), and more preventive care visits. The higher levels of preventive services are likely to reduce morbidity and mortality from preventable diseases. Also, as more patients come for their allotted appointments, the practice can increase its visit capacity and reduce its costs, particularly those associated with the inefficient use of clinician and staff time when slots are wasted.

Recently, advances have been made in immunization computer systems to include additional processing features. However, these advances have come at a cost of additional processing overhead, and inadequate intelligence within the system to capture features that may be important for system operation. Furthermore, conventional systems require users to scroll across a grid display and manually search for items across an array, causing cognitive load on the user.

SUMMARY

Various apparatus, systems and methods are disclosed herein relating to an efficient immunization computer interface.

In some illustrative embodiments, a system is disclosed for generating a computer interface for an immunization regimen, comprising: a processing apparatus; a memory operatively coupled to the processing apparatus, the memory configured to store immunization data itemsets and medical data itemsets; and a data display control module; wherein the processing apparatus is configured to determine a frequency of immunization data and medical data itemsets associated with a rule for an immunization regimen, calculate proportions of the itemsets for the immunization regimen; calculate a confidence factor for a least some of the calculated proportions, comprising an estimate of the probability a rule portion of a rule includes another rule portion, generate a computer interface via the data display control module, comprising immunization regimen data based on the confidence factor, wherein the immunization regimen data comprises expected frequencies of immunization data.

In some illustrative embodiments, a processor-based method is disclosed for generating a computer interface for an immunization regimen in a processing apparatus, comprising: receiving, in a memory, immunization data itemsets and medical data itemsets; and determining, via a processing apparatus, a frequency of immunization data and medical data itemsets associated with a rule for an immunization regimen, calculating, via the processing apparatus, proportions of the itemsets for the immunization regimen; calculating, via the processing apparatus, a confidence factor for a least some of the calculated proportions, comprising an estimate of the probability a rule portion of a rule includes another rule portion, and generating a computer interface via a data display control module coupled to the processing apparatus, wherein the computer interface comprises immunization regimen data based on the confidence factor, wherein the immunization regimen data comprises expected frequencies of immunization data.

In some illustrative embodiments, a system is disclosed for generating a computer interface for an immunization regimen, comprising: a processing apparatus; a memory operatively coupled to the processing apparatus, the memory configured to store immunization data itemsets and medical data itemsets; and a data display control module; wherein the processing apparatus is configured to determine a frequency of immunization data and medical data itemsets associated with a rule for an immunization regimen, calculate proportions of the itemsets for the immunization regimen; calculate a confidence factor for a least some of the calculated proportions, comprising an estimate of the probability a rule portion of a rule includes another rule portion, generate a computer interface via the data display control module, the computer interface comprises immunization regimen data comprising only the immunization regimen data that meets or exceeds the confidence factor, wherein the immunization regimen data comprises expected frequencies of immunization data, and wherein the processing apparatus is configured to generate the computer interface utilizing interface graphics module templates that are based on the confidence factor for a least some of the calculated proportions . . .

BRIEF DESCRIPTION OF THE FIGURES

The present invention is illustrated by way of example and not limitation in the figures of the accompanying drawings, in which like references indicate similar elements and in which:

FIG. 5 shows an illustration of a simplified itemset of a plurality of immunization regimens of a plurality (e.g., 3) immunization vaccines and a plurality (e.g., 2) of medical data items under sn illustrative embodiment;

FIGS. 8A-8C show examples of interfaces that may be produced using the embodiments of FIGS. 1-3 under an illustrative embodiment.

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that he programming techniques and hardware arrangements disclosed herein, embodied on tangible mediums, are configured to transform the conventional hardware components into new machines that operate more efficiently (e.g., providing greater and/or more robust data, while using less processing overhead and/or power consumption) and/or provide improved user interfaces for human-machine interaction.

Figure 1:
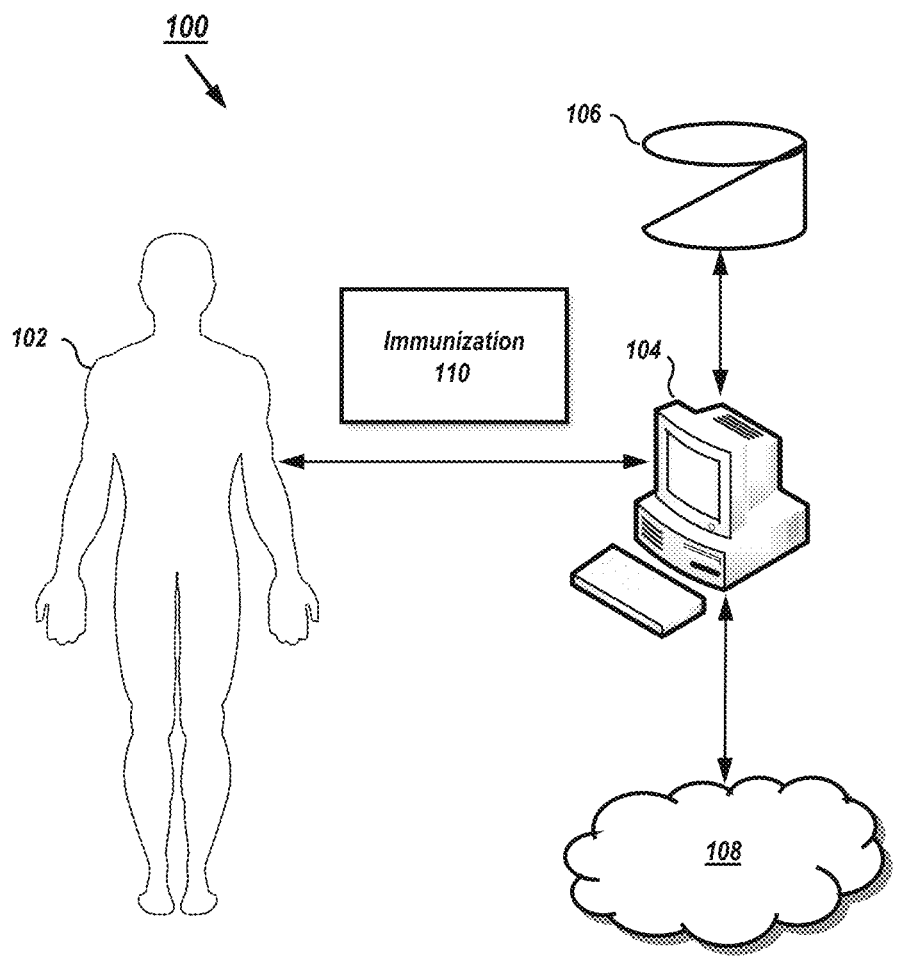
FIG. 1 illustrates a simplified overview of a processor-baed immunization monitoring system including sensors, a portable device, and a processing apparatus communicatively coupled to a network under an illustrative embodiment.

Turning to FIG. 1, a system 100 is shown for collecting and processing data from immunization data 110 obtained from a patient 102. In this example, immunization data 110 may be obtained from radio frequency identification (RFID) tags that are affixed to respective immunization delivery devices (e.g., syringe, container, etc.). Alternately, immunization data may be obtained via manual entry by a healthcare provider. Immunization data 110 may comprise information relating to a specific vaccination being administered (e.g., hepatitis, Human papillomaviruses (HPV), polio, MMR, etc.), along with an immunization type/route (e.g., Inactivated Bacterial Toxoids/IM, Recombinant Viral/IM, Live Viral/Oral (tablets), etc.), as well as trade names of vaccinations (e.g., Pediarix®, Recombivax HB®, etc.) and related administrative data (e.g., age range 18 through 65 years, approved for $5^{th}$ (DTaP) and $4^{th}$ (IPV) booster at 4-6 years, 3-dose primary series, etc.).

Immunization data 110 may be transmitted and/or entered into processing device 104. Processing device 104 may be operatively coupled to a database 106, that may be configured to store immunization data 110, along with medical data (see FIG. 4) pertaining to one or more patients. Database 106 may be configured as a relational database or any other suitable database for processing data. Processing device 104 may be operatively coupled to network 108, which may be configured as a large area network (LAN), wide area network (WAN), or any other suitable network. In the embodiment of FIG. 1, database 106 is shown as a stand-alone database. However, those skilled in the art will appreciated that database 106 may be integrated into processing device 104, and/or located in the network 108. Database 106 may also be configured as part of a distributed database network, comprising a plurality of databases connected through network 108.

Figure 2:
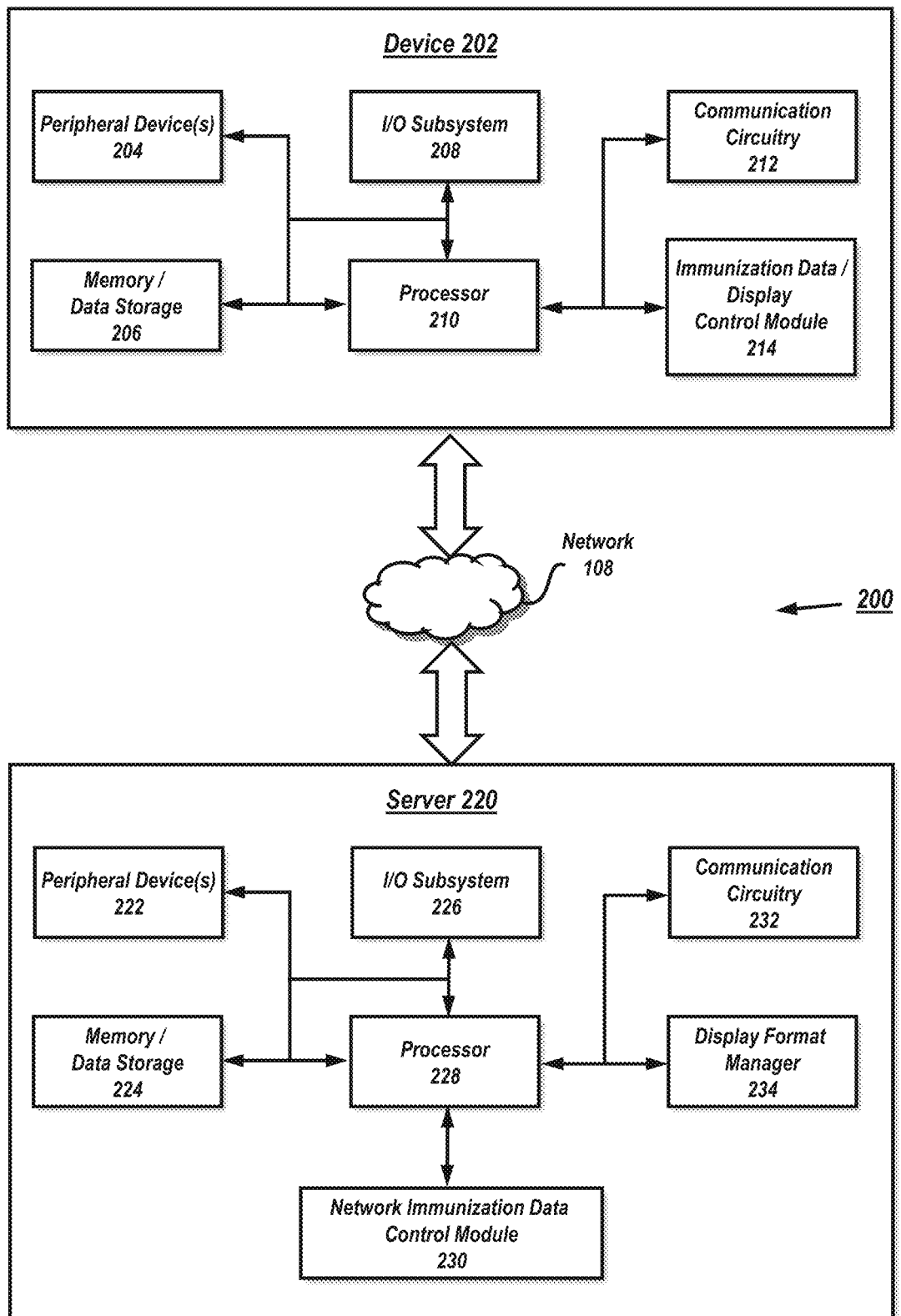
FIG. 2 schematically illustrates an operating environment for a portable device and a server communicatively coupled to a network for processing data under an illustrative embodiment.

FIG. 2 shows an operating environment for system 200 that includes a processing device 202, which may be configured as device 104, and a server 220 communicating via the network 108, wherein the system is configured to process immunization data and medical data under an illustrative embodiment. In the illustrative embodiment, the processing device 202 includes a processor 210 or processor circuit, one or more peripheral devices 204, memory/data storage 206, communication circuitry 212, and a immunization data and display control module 214. Immunization data and display control module 214 may be configured to process and/or manage immunization data and/or medical data as described in greater detail below. The immunization data and display control module 214 may be incorporated into memory/data storage 206 with or without a secure memory area, or may be a dedicated component, or incorporated into the processor 210. Of course, processing device 202 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 206, or portions thereof, may be incorporated in the processor 210 in some embodiments.

The processor 210 may be embodied as any type of processor currently known or developed in the future and capable of performing the functions described herein. For example, the processor 210 may be embodied as a single or multi-core processor(s), digital signal processor, microcontroller, or other processor or processing/controlling circuit. Similarly, memory/data storage 206 may be embodied as any type of volatile or non-volatile memory or data storage currently known or developed in the future and capable of performing the functions described herein. In operation, memory/data storage 206 may store various data and software used during operation of the processing device 210 such as access permissions, access parameter data, operating systems, applications, programs, libraries, and drivers.

Memory/data storage 206 may be communicatively coupled to the processor 210 via an I/O subsystem 208, which may be embodied as circuitry and/or components to facilitate input/output operations with the processor 210, memory/data storage 206, and other components of the processing device 202. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 210, memory/data storage 206, and other components of the processing device 202, on a single integrated circuit chip.

The processing device 202 includes communication circuitry 212 (communication interface) that may include any number of devices and circuitry for enabling communications between processing device 202 and one or more other external electronic devices and/or systems. Similarly, peripheral devices 204 may include any number of additional input/output devices, interface devices, and/or other peripheral devices. The peripheral devices 204 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 220 may be embodied as any type of server (e.g., a web server, etc.) or similar computing device capable of performing the functions described herein. In the illustrative embodiment of FIG. 2 the server 220 includes a processor 228, an I/O subsystem 226, a memory/data storage 224, communication circuitry 232, and one or more peripheral devices 222. Components of the server 220 may be similar to the corresponding components of the processing device 202, the description of which is applicable to the corresponding components of server 220 and is not repeated herein for the purposes of brevity.

The communication circuitry 232 of the server 220 may include any number of devices and circuitry for enabling communications between the server 220 and the processing device 202. In some embodiments, the server 220 may also include one or more peripheral devices 222. Such peripheral devices 222 may include any number of additional input/output devices, interface devices, and/or other peripheral devices commonly associated with a server or computing device. The server 220 also includes a network immunization data control module 230 that is configured to process sensor data for the immunization data and display control module 214. The processing from network immunization data control module 230 may be configured as back-end processing, and/or may be configured to further process sensor data processed and/or pre-processed in immunization data and display control module 214. Display format manager 234 is also operatively coupled to processor 228 and may be configured to format screens for device 202 based on data processed in the network immunization data control module 230. In some illustrative embodiments, network immunization data control module 230 and display format manager 234 may be integrated with immunization data and display control module 214 to operate solely on device 202.

In the illustrated embodiment, communication between the server 220 and the processing device 202 takes place via the network 108 that may be operatively coupled to one or more network switches (not shown). In one embodiment, the network 108 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 202 and the communication circuitry 232 of the server 220 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 108 may include any number of additional devices, such as additional computers, routers, and switches, to facilitate communications between the processing device 202 and the server 220.

Figure 3:
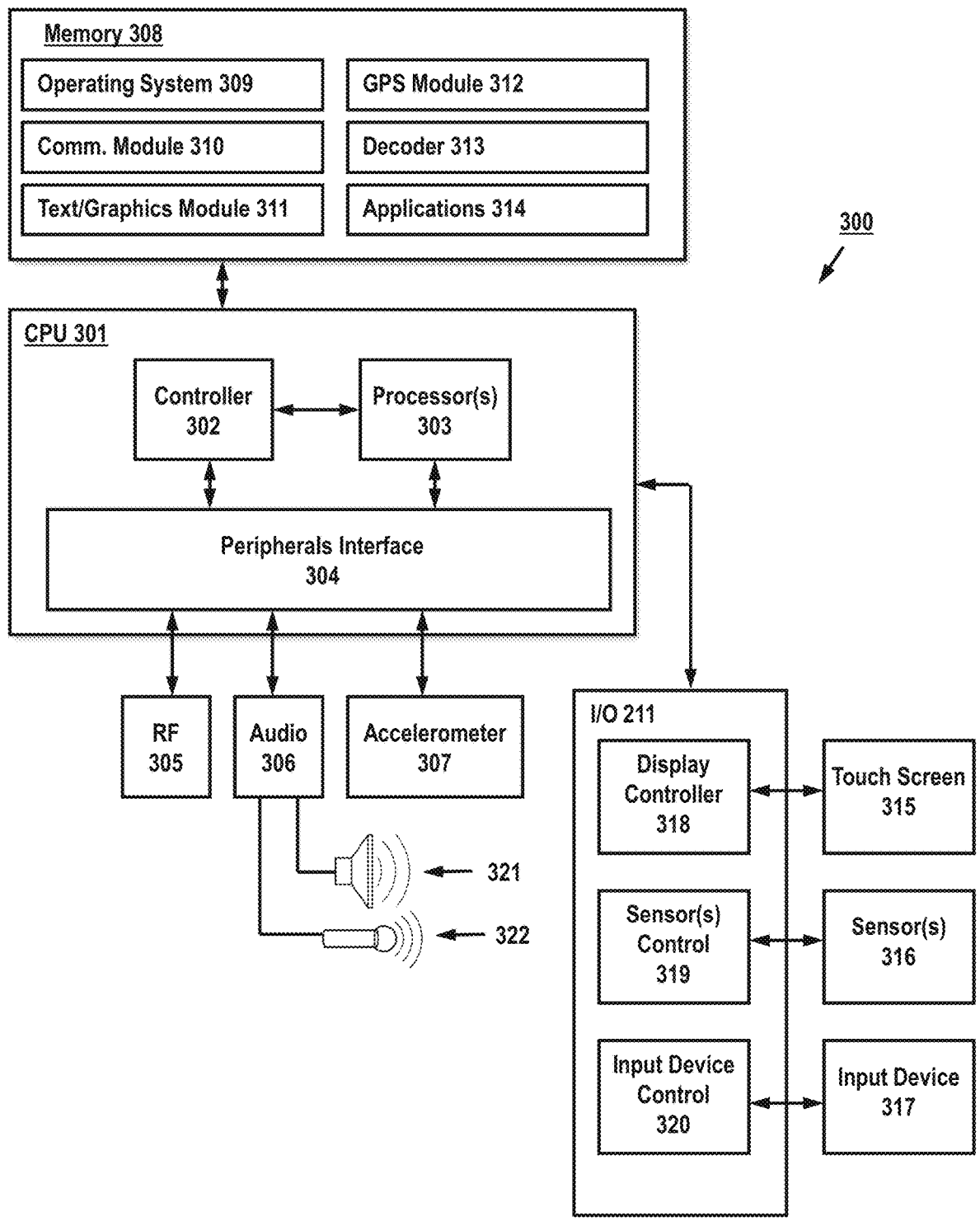
FIG. 3 schematically illustrates an operating environment for a portable device configured to process data under an illustrative embodiment.

FIG. 3 is an exemplary embodiment of a computing device 300 (such as processing device 104), and may be a personal computer, smart phone, tablet computer, laptop and the like. Device 300 may include a central processing unit (CPU) 301 (which may include one or more computer readable storage mediums), a memory controller 302, one or more processors 303, a peripherals interface 304, RF circuitry 305, audio circuitry 306, accelerometer 307, speaker 321, microphone 322, and input/output (I/O) subsystem 221 having display controller 318, control circuitry for one or more sensors 319 and input device control 320. These components may communicate over one or more communication buses or signal lines in device 300. It should be appreciated that device 300 is only one example of a portable multifunction device, and that device 300 may have more or fewer components than shown, may combine two or more components, or a may have a different configuration or arrangement of the components. The various components shown in FIG. 3 may be implemented in hardware or a combination of hardware and software, including one or more signal processing and/or application specific integrated circuits.

Memory (or storage) 308 may include high-speed random access memory (RAM) and may also include non-volatile memory, such as one or more magnetic disk storage devices, flash memory devices, or other non-volatile solid-state memory devices. Access to memory 308 by other components of the device 300, such as processor 303, and peripherals interface 304, may be controlled by the memory controller 302. Peripherals interface 304 couples the input and output peripherals of the device to the processor 303 and memory 308. The one or more processors 303 run or execute various software programs and/or sets of instructions stored in memory 308 to perform various functions for the device 300 and to process data. In some embodiments, the peripherals interface 304, processor(s) 303, decoder 313 and memory controller 302 may be implemented on a single chip, such as a chip 301. In other embodiments, they may be implemented on separate chips.

RF (radio frequency) circuitry 305 receives and sends RF signals, also known as electromagnetic signals. The RF circuitry 305 converts electrical signals to/from electromagnetic signals and communicates with communications networks and other communications devices via the electromagnetic signals. The RF circuitry 305 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 305 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VOIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 306, speaker 321, and microphone 322 provide an audio interface between a user and the device 300. Audio circuitry 306 may receive audio data from the peripherals interface 304, converts the audio data to an electrical signal, and transmits the electrical signal to speaker 321. The speaker 321 converts the electrical signal to human-audible sound waves. Audio circuitry 306 also receives electrical signals converted by the microphone 321 from sound waves, which may include utterances from a speaker. The audio circuitry 306 converts the electrical signal to audio data and transmits the audio data to the peripherals interface 304 for processing. Audio data may be retrieved from and/or transmitted to memory 308 and/or the RF circuitry 305 by peripherals interface 304. In some embodiments, audio circuitry 306 also includes a headset jack for providing an interface between the audio circuitry 306 and removable audio input/output peripherals, such as output-only headphones or a headset with both output (e.g., a headphone for one or both cars) and input (e.g., a microphone).

I/O subsystem 221 couples input/output peripherals on the device 300, such as touch screen 315, sensors 316 and other input/control devices 317, to the peripherals interface 304. The I/O subsystem 221 may include a display controller 318, sensor controllers 319, and one or more input controllers 320 for other input or control devices. The one or more input controllers 320 receive/send electrical signals from/to other input or control devices 317. The other input/control devices 317 may include physical buttons (e.g., push buttons, rocker buttons, etc.), dials, slider switches, joysticks, click wheels, and so forth. In some alternate embodiments, input controller(s) 320 may be coupled to any (or none) of the following: a keyboard, infrared port, USB port, and a pointer device such as a mouse, an up/down button for volume control of the speaker 321 and/or the microphone 322. Touch screen 315 may also be used to implement virtual or soft buttons and one or more soft keyboards.

Touch screen 315 provides an input interface and an output interface between the device and a user. Display controller 318 receives and/or sends electrical signals from/to the touch screen 315. Touch screen 315 displays visual output to the user. The visual output may include graphics, text, icons, video, and any combination thereof. In some embodiments, some or all of the visual output may correspond to user-interface objects. Touch screen 315 has a touch-sensitive surface, sensor or set of sensors that accepts input from the user based on haptic and/or tactile contact. Touch screen 315 and display controller 318 (along with any associated modules and/or sets of instructions in memory 308) detect contact (and any movement or breaking of the contact) on the touch screen 315 and converts the detected contact into interaction with user-interface objects (e.g., one or more soft keys, icons, web pages or images) that are displayed on the touch screen. In an exemplary embodiment, a point orf contact between a touch screen 315 and the user corresponds to a finger of the user. Touch screen 215 may use LCD (liquid crystal display) technology, or LPD (light emitting polymer display) technology, although other display technologies may be used in other embodiments. Touch screen 315 and display controller 318 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 315.

Device 300 may also include one or more sensors 316 such as heart rate sensors, touch sensors, optical sensors that comprise charge-coupled device (CCD) or complementary metal-oxide semiconductor (CMOS) phototransistors. The optical sensor may capture still images or video, where the sensor is operated in conjunction with touch screen display 315. Device 300 may also include one or more accelerometers 307, which may be operatively coupled to peripherals interface 304. Alternately, the accelerometer 307 may be coupled to an input controller 320 in the I/O subsystem 221. The accelerometer is preferably configured to output accelerometer data in the x, y, and z axes.

In some illustrative embodiments, the software components stored in memory 308 may include an operating system 309, a communication module 310, a text/graphics module 311, a Global Positioning System (GPS) module 312, decoder 313 and applications 314. Operating system 309 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 310 facilitates communication with other devices over one or more external ports and also includes various software components for handling data received by the RF circuitry 305. An external port (e.g., Universal Serial Bus (USB), Firewire, etc.) may be provided and adapted for coupling directly to other devices or indirectly over a network (e.g., the Internet, wireless LAN, etc.).

Text/graphics module 311 includes various known software components for rendering and displaying graphics on the touch screen 315, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 312 determines the location of the device and provides this information for use in various applications. Applications 314 may include various modules, including health monitoring software, sensor software, navigation software, mapping, address books/contact list, email, instant messaging, and the like.

Figure 4:
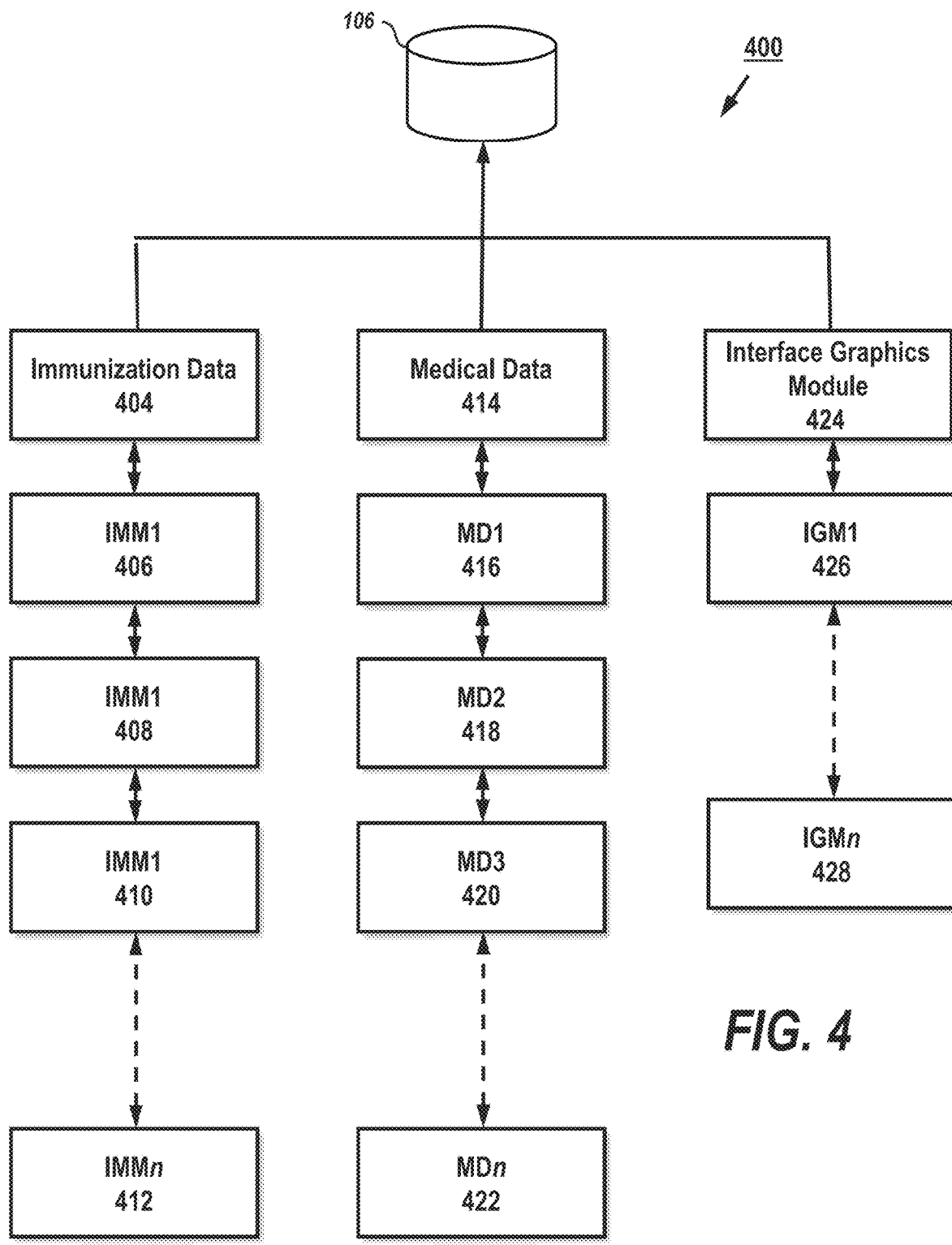
FIG. 4 shows an operating environment for a database with respect to storage and processing, via one or more processors, of immunization and/or medical data under an illustrative embodiment.

Turning to FIG. 4, the figure illustrates an operating environment 400 for database 106 with respect to storage and processing (via processor(s) 210, 228 and/or 303) of immunization and/or medical data. Under an illustrative embodiment, immunization data 404 comprises information relating to a specific vaccination being administered, an immunization type/route, as well as trade names of vaccinations and related administrative data (see discussion relating to immunization data 110, above). Each of these data items may be stored as individual data items IMM1-IMMn (406-412) as shown in the figure. In some illustrative embodiments, data items IMM1-IMMn (406-412) are configured as abstract data types and configured as hierarchical tree structures, having a plurality of different root values and subtrees of children with a parent node, represented as a set of linked nodes. In some illustrative embodiments, the data types may be configured recursively (and/or mutually recursive) to be defined as a value, together with a list of trees and subtrees of its children.

In some illustrative embodiments, data items IMM1-IMMn (406-412) are configured as an array data structure. The array can be configured as a nested hierarchy of containers, where the nesting depth determines its number of dimensions, or dimensionality. For example, a one-dimensional array of values is a container of values; a two-dimensional array of values is a container of one-dimensional arrays of values; a three-dimensional array of values is a container of two-dimensional arrays of values; and so on. Arrays contained within another array may be considered subarrays. Thus, a two-dimensional array has one-dimensional subarrays and similarly a three-dimensional array has two-dimensional and one-dimensional subarrays. The immediate subarrays of an array with dimensionality two or greater are the immediately contained subarrays. Such configurations may be constructed by augmenting the language of the Standard Library (e.g., C++ Standard Library) containers with terminology that reflects the more robust structure of arrays. Also, the standard notions of values and value type may be augmented using elements and element type.

Each value of the array may be associated with an index. Likewise, each element of an N-dimensional array may an associated sequence of N indices. The index may comprise an integral value that uniquely specifies a value in the array. If n is a valid index into an array, the notation A[n] may be used to refer to the value associated with that index. Indices may be determined by the index bases of the array. Index bases are a list of integral values, one for each dimension, that specify the least valid index for a dimension. For instance, a 3×4 array with index bases {0, 0} has as valid indices 0 through 2 for the first dimension and 0 through 3 for the second dimension. An array A with the above index bases addresses its first value as A [0]. The first value of this first value is A[0][0], and so on. In some illustrative embodiments, the array hierarchical structure may be mapped to a flat memory model. In one example, one-dimensional arrays are stored as contiguous blocks of memory. Then, N-dimensional arrays are stored as contiguous blocks of pointers to (N−1)-dimensional arrays. In another example, the model stores all array elements in a single block of memory.

Under an illustrative embodiment, medical data 414 comprises information comprising data items MD1-MDn (416-422) relating to specific patients and related socioeconomic, environmental, biomedical, and genetic factors; individual health status and health behaviors; biomedical and genetic factors, as well as resource use, outcomes, financing, and expenditures. These data may be stored in database 106 and may further be requested and received from a variety of electronic health records (EHRs), personal medical records, disease registries, and other databases. Each of these data items 416-422 may be stored as individual data items MD1-MDn (416-422) as shown in the figure. In some illustrative embodiments, data items MD1-MDn (416-422) are configured as abstract data types and configured as hierarchical tree structures, having a plurality of different root values and subtrees of children with a parent node, represented as a set of linked nodes, similar to immunization data 404, discussed above. In some illustrative embodiments, data items MD1-MDn (416-422) are configured as an array data structure, similar to immunization data 404, discussed above.

Under an illustrative embodiment, interface graphics module 424 comprises a plurality of interface graphics module templates IGM1-IGMn (426-428) that function to generate data to form an immunization display screen (FIGS. 8A-8C) that is optimized to display efficiently on the computer system and to generate a screen that provides necessary immunization data without requiring the need for scrolling. In some illustrative embodiments, the interface graphics module 424 selects one or more templates IGM1-IGMn (426-428) based on the results provided by the processor(s) 210, 228 and/or 303 after processing the immunization data 404 and/or medical data 414. Each template (420-422) may be configured as a display structure that formats the specific immunization display screen. As part of its template processing, interface graphics module 424 performs minification on the display data to optimize the displayed data. In one example, the minification includes the removal of all unnecessary characters in the source code, without changing its functionality. Such unnecessary characters may include white space characters, new line characters and block delimiters that are used to add readability to the code, but is not necessary for it to execute. The minification advantageously provides a minified source that can be interpreted immediately without the need for decompression, and allows the same interpreter to work with the original, as well as the minified source.

In addition, the interface graphics module 424 provides display data for the processing data from processor(s) 210, 228 and/or 303 that includes flags for data indicating a borderline or out-of-bounds condition for the immunization data. The flags may be further associated with alerts or warning in the immunization system.

Immunization data 404 and medical data 414 may be subjected to data mining as part of the processing in the system (100, 200). In some illustrative embodiments, the system (100, 200) may be configured with a rules system to associate immunizations and medical data. For example, rules may be generated for specific immunization regimens and medical conditions, e.g., {IMM1}→ {Rotavirus1};
{IMM1$_1$, IMM2$_1$, IMM3$_2$}→ {Rotavirus1}; and
{IMM1$_{2mo}$, IMM2$_{4mo}$, IMM3$_{6mo}$}→{Rotavirus1} where IMM1 represent a vaccine (e.g., RV5) for a first Rotavirus regimen, IMM1$_1$, IMM2$_1$, IMM3$_2$. represent a type/route for the first Rotavirus regimen, and {IMM1$_{2mo}$, IMM2$_{4mo}$, IMM3$_{6mo}$} represent administrative data, indicating administration at 2 months, 4 months and 6 months. A similar configuration may be done for medical data (e.g., {MD1, MD2, MD3, MD4}→{Patient1}). The immunization data and medical data rules may be nested relative to themselves and each other, meaning that an immunization regimen may comprise a plurality of sub-regimens, and the immunization regimen and sub-regimens may be associated or linked with medical data and medical data items (subparts).

In a simplified example, the rules may be configured for association rule mining. In one example, let $M=\{m_1, m_2, \ldots m_n\}$ be a set of n attributes, or items. The items may be binary or some other suitable value. Let $I=\{i_1, i_2, \ldots i_n\}$ be a set of regimens. Rach regimen I may have a unique ID and contain a subset of items in M. A rule may be defined as an implication of the form $X \rightarrow Y$ where X, $Y \subseteq I$ and $X \cap Y = 0$. THe sets of items X and Y may be considered antecedent (LHS) and consequent (RHS) of the rule, respectively.

FIG. 5 shows an illustration of a simplified itemset 500 of a plurality of immunization regimens 504 (1-7) of three immunization vaccines Imm1-Imm3 (506-510) and two medical data items MD1-MD2 (512-514). In this simplified example, 1 represents the presence of an item, while 0 represents an absence of the item. Thus, it can be seen that, Imm3 is present only if Imm1 or Imm2 are present, but not both. Conversely, Imm3 is absent if both Imm1 and Imm2 are present. Furthermore, Imm3 is present if both Imm1 and Imm2 are absent. Similarly, medical data item MD1 is present if Imm2 is present. Medical data item MD2 is present if Imm1 is present.

To obtain rules from all of the sets of possible rules, constraints on various measures of significance and interest can be used. Exemplary constrains may include minimum thresholds on support and confidence. The support (supp) of an itemset may be defined as the proportion of regimens in the data set that contain the itemset. Using the example of FIG. 5, use of Imm1 and Imm2 without use of Imm3 has a support of 2/7 or 0.29, since it occurs in 29% of all regimens. The confidence (conf) of a rule may be defined as conf $(X \rightarrow Y) = \text{supp}(X \cup Y)/\text{supp}(X)$. The confidence may be interpreted as an estimate of the probability $P(Y|X)$, or the probability of finding the RHS of the rule for a regimen under the condition that the regimen also contains the LHS.

The lift of a rule may be defined as lift $(X \rightarrow Y) = [\text{supp}(X \cup Y)/\text{sup}(X)]/[\text{sup}(Y)*\text{sup}(X)]$, and the conviction (conv) of a rule may be defined as conv $(X \rightarrow Y) = [1-\text{supp}(Y)]/[1-\text{conf}(X \rightarrow Y]$. The conviction of the rule $X \rightarrow Y$ can be interpreted as the ratio of the expected frequency that X occurs without Y. In other words, this can be considered the frequency that the rule makes an incorrect prediction if X and Y were independent divided by the observed frequency of incorrect predictions.

Rule generation association may be performed utilizing a plurality of steps. First, minimum support is applied to find all frequent itemsets in a database. Next, these frequent itemsets and the minimum confidence constraint may be used used to form rules. In some illustrative embodiments, particularly when itemsets are relatively small, finding all frequent itemsets in a database may simply involve searching all possible itemsets and item combinations. Typically, the set of possible itemsets is the power set over/and has size 2n−1. Although the size of the powerset grows exponentially in the number of items n in I, efficient search is possible using the downward-closure property of support (also known as anti-monotonicity) that guarantees that, for a frequent itemset, all its subsets are also frequent and thus for an infrequent itemset, all its supersets must also be infrequent. Using this property, efficient algorithms (e.g., Apriori, FP-growth, Eclat) can find all frequent itemsets. Typically, for association rule mining, given a set of itemsets, the algorithm attempts to find subsets that are common to at least a minimum number of the itemsets. Using a "bottom up" approach, such as in Apriori, frequent subsets may be extended one item at a time (candidate generation), and groups of candidates are tested against the data. The algorithm terminates when no further successful extensions are found.

Utilizing apriori techniques, a breadth-first search and a tree structure may be used to count candidate item sets efficiently. In the exemplary embodiment, candidate item sets may be generated of length k from item sets of length k−1. The candidates having an infrequent sub-pattern may then be pruned. According to the downward closure lemma, the candidate set contains all frequent k-length item sets. After that, it scans the database to determine frequent item sets among the candidates.

Using the above-referenced techniques, immunization data and medical data may be processed to generate a customized interface containing the most statistically relevant data relating to an immunization regimen. Because this data is streamlined before the interface is generated, the processing device does not require as many resources to generate the interface. Additionally, since the interface is additionally processed to be graphically depicted in a single screen, graphical resources are preserved, while providing an improved visual depiction of an immunization regimen for a healthcare service provider.

Figure 6:
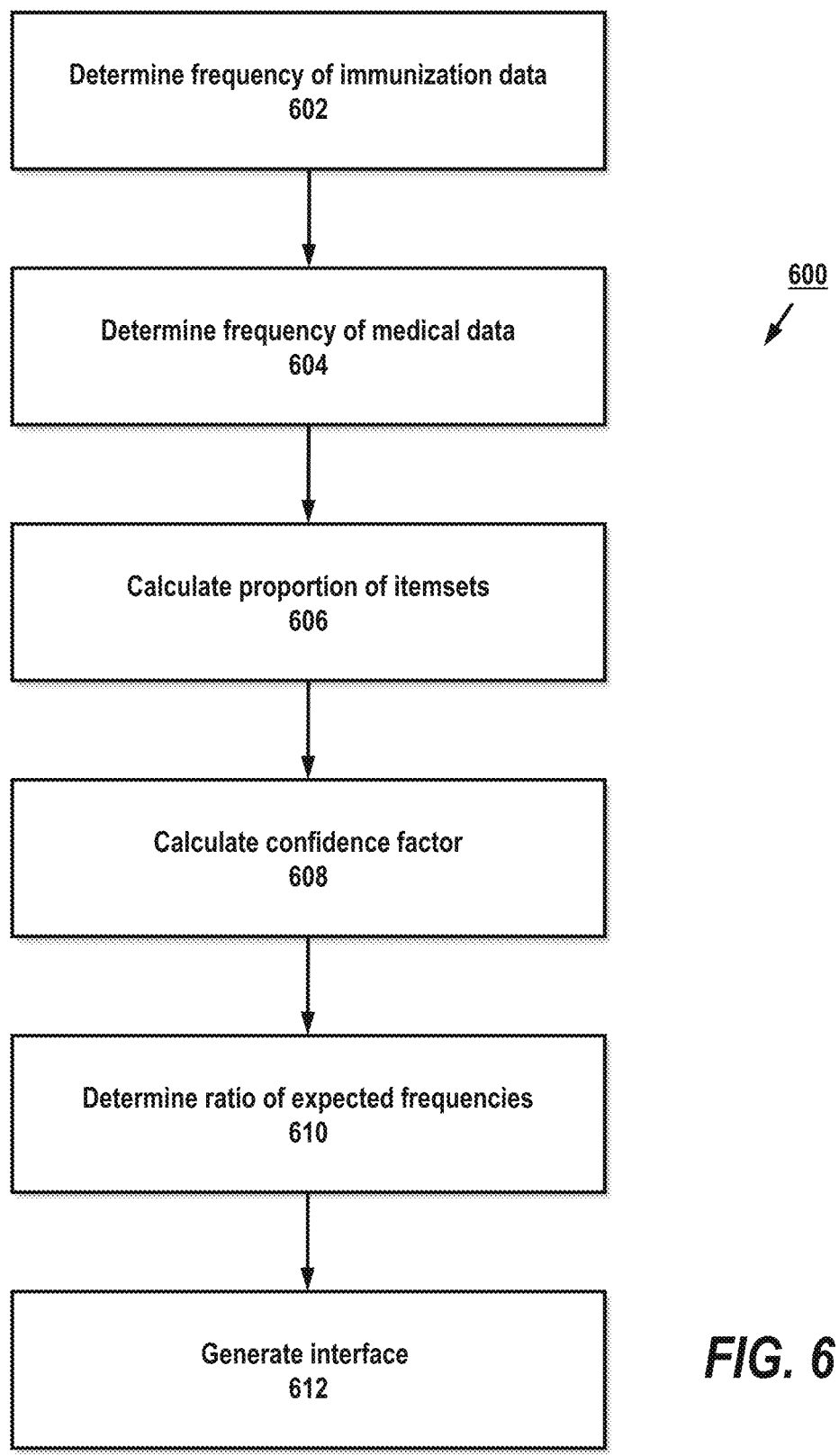
FIG. 6 shows an exemplary process for generating an efficient immunization interface using the techniques described herein under an illustrative embodiment.

Turning to FIG. 6, an exemplary process 600 is disclosed for generating an efficient immunization interface using the techniques described above. In block 602, the system (e.g., 100, 200) determines a frequency of immunization data. This frequency may include, but is not limited to a presence or absence of itemsets in the immunization database (e.g., 106). In block 604, the system (e.g., 100, 200) determines the frequency of medical data. Similar to block 602, the frequency may include, but is not limited to a presence or absence of itemsets in the medical data database (e.g., 106).

In block 606, the system (e.g., 100, 200) calculates proportions for itemsets. The proportion may be calculated similarly as a support (supp) of itemsets, which calculates proportion of regimens in the data set that contain the itemset. In block 608, the system may calculate a confidence factor. As explained above, the confidence (conf) may comprise an estimate of the probability of finding a portion (e.g., RHS) of a rule for a regimen under the condition that the regimen also contains the other portion (LHS). In block 610, the system determines a ratio of expected frequencies, which may be executed using a conviction of the rule applied to the immunization and medical data. In block 612, the system generates a graphical interface representing the processing of method 600

Using the techniques of the present disclosure, once an immunization regimen is selected for a patient, the system processes the regimen using immunization data and medical data to predict optimal follow-up immunization, related immunization, alerts, warnings, and the like. In addition, depending on the predicted data, the system generates a customized interface representing the data produced from process 600.

Figure 7:
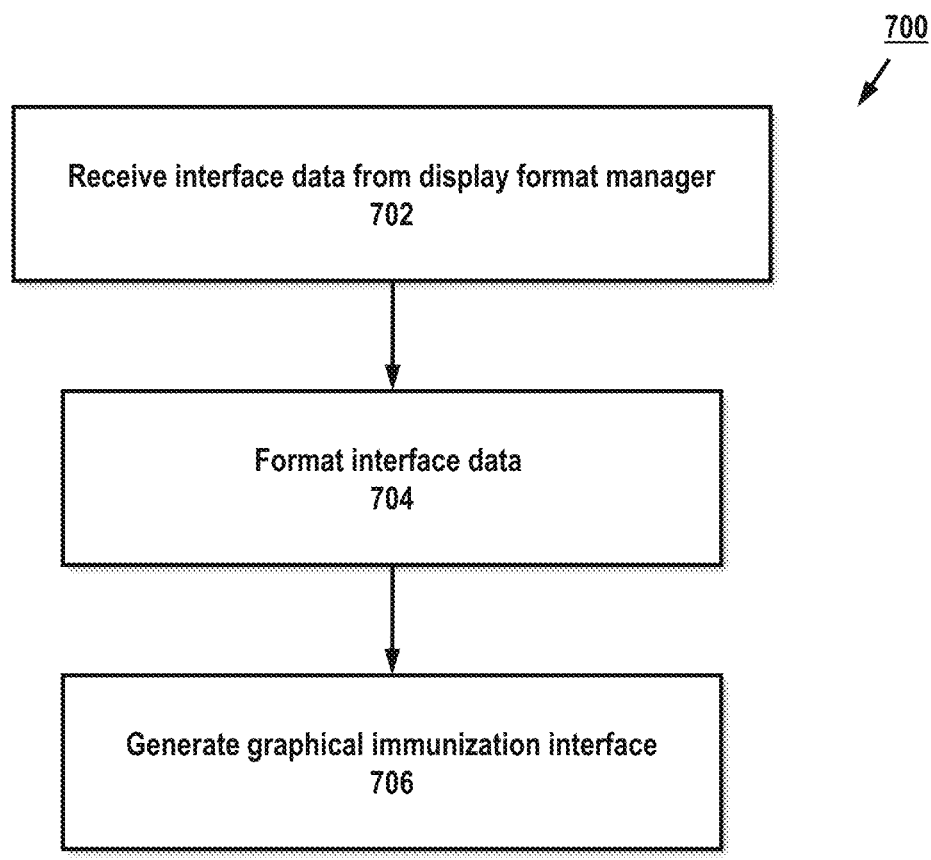
FIG. 7 illustrates a process for generating a graphical immunization interface under an illustrative embodiment.

Turning to FIG. 7, the figure illustrates a process 700 for generating a graphical immunization interface under an illustrative embodiment. The process 700 may be executed using modules 214 and/or 234, discussed above. In block 702, the display format manager 234 provides interface data that is received in immunization data display control module 214. In some illustrative embodiments, the immunization data display control module 214 may be configured to generate the interface data. In block 704, the immunization data display control module 214 formats the interface data and generates a graphical immunization interface in block 706.

Figure 8A:
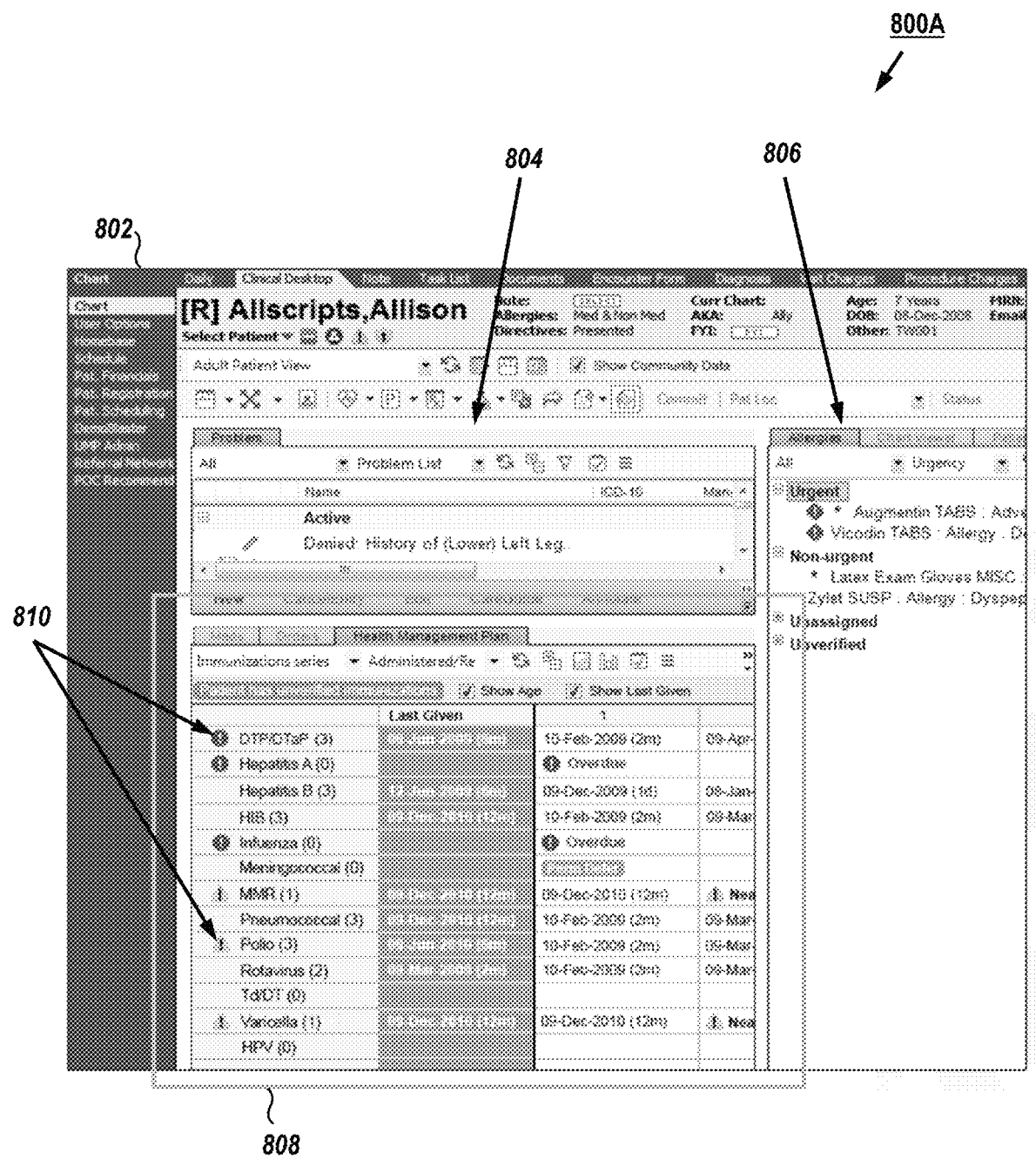
Figure 8B:
Figure 8C:
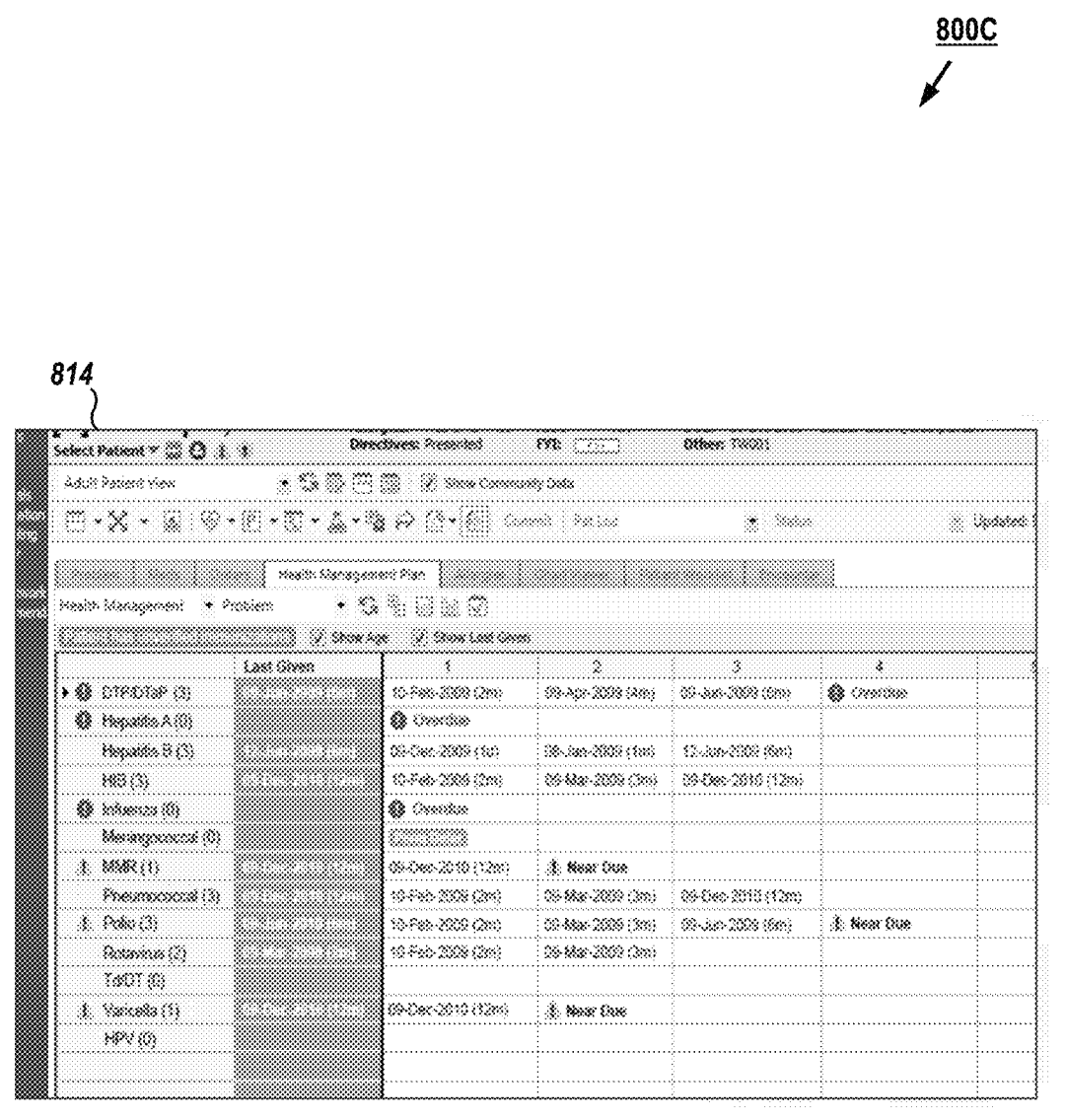

FIGS. 8A-8C show examples of interfaces (800A-800C) that may be produced under the present disclosure. In FIG. 8A, the interface is provided in the context of an application 802 executed on a processing device (e.g., 104) The examples of FIG. 8A-8C show a split-screen example, which segregates the screen into different panels (804-808). However, it is understood by those skilled in the art that the screen panels may be combined in various ways, depending on the necessary application. One or more of the panels (804-808) may be subjected to minification to provide efficient rendering of the panels, and one or more of the panels are subjected to the predictive processing described above in connection with FIGS. 4-7 to provide only the necessary to data to evaluate the immunization regimen. Also, depending on the predictive processing described above, various warnings/alerts (810) may be provided to allow a health care provider to take the necessary action. In some illustrative embodiments, the presence of a warning/alert may cause a panel (e.g., 808) to overlap the others in the display (or full screen vie), to provide additional emphasis to the interface.

In the example of FIG. 8B, an interface 808B, executed within an application 812 may provide further information 814 regarding a specific portion of an immunization regimen that is derived from the immunization data and/or medical data. The further information may comprise predictive data associated with the medical data and/or immunization data. For example, if a particular immunization was declined, the system may process the medical data and/or immunization data to determine other vaccinations that will be declined. In other examples, alternate vaccinations may be provided having the highest likelihood that the declining patient would accept the alternate vaccination. FIG. 8C illustrates an embodiment where the interface 800C is established as a full screen view within application 814.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A system for generating an optimized computer interface for a medical computer system, comprising:
    a processing apparatus;
    a memory operatively coupled to the processing apparatus, the memory configured to store a nested hierarchy of first data itemsets and second itemsets configured as an array data structure;
    an interface graphics module, comprising a plurality of interface graphics module templates configured to format one or more display structures; and
    a data display control module;
    wherein the processing apparatus is configured to
        associate first data itemsets and second itemsets with one or more rules comprising a plurality of rule portions for executing a regimen;
        apply a first constraint utilizing proportions of the itemsets for the regimen;
        apply a second constraint utilizing a confidence factor, wherein the confidence factor represents an estimate of the probability of a rule portion being associated with another rule portion, thereby reflecting the statistical relevance of the data;
        select one or more of the interface graphic module templates based on the applied first constraint and second constraint;
        perform minification on the selected one or more interface graphic module templates, wherein the minification optimizes display data by removing extraneous code elements that do not affect functionality, thereby reducing file size and enhancing rendering efficiency; and
        execute the minified one or more interface graphic module templates to format display structures, minimizing required scrolling for the computer interface and reducing processing overhead via the data display control module.

2. The system of claim 1, wherein the processing apparatus is configured to generate the optimized computer interface via the display control module utilizing only the regimen data that meets or exceeds the confidence factor.

3. The system of claim 1, wherein the processing apparatus is configured to calculate proportions of the itemsets utilizing a hierarchical tree structure for the first data and second data itemsets.

4. The system of claim 1, wherein the first data itemsets comprise information relating to a specific vaccination being administered, an first type/route, trade names of vaccinations, and administrative data relating to the regimen.

5. The system of claim 4, wherein the second itemsets comprises data relating to at least two of specific patients and related socioeconomic, environmental, biomedical factors, genetic factors, individual health status and health behaviors, biomedical and genetic factors, and at least one of resource use, outcomes, financing, and expenditures.

6. The system of claim 1, wherein the processing apparatus is configured to generate the optimized computer interface utilizing the interface graphics module templates that are based on the confidence factor for a least some of the calculated proportions.

7. A processor-based method for generating an optimized computer interface for a medical computer system, comprising:
    receiving, in a memory, a nested hierarchy of first data itemsets and second itemsets configured as an array data structure;
    accessing a plurality of interface graphics module templates configured to format one or more display structures, and comprising data structure formats associated with the first data itemsets and second itemsets;
    associating, via a processing apparatus, first data itemsets and second itemsets with one or more rules comprising a plurality of rule portions for a regimen;
    applying, via the processing apparatus, a first constraint utilizing proportions of the itemsets for the regimen;
    applying, via the processing apparatus, a second constraint utilizing a confidence factor, wherein the confidence factor represents an estimate of the probability of a rule portion being associated with another rule portion, thereby reflecting the statistical relevance of the data;
    selecting one or more of the interface graphic module templates based on the applied first constraint and second constraint;
    performing minification on the selected one or more interface graphic module templates, wherein the minification optimizes display data by removing extraneous code elements that do not affect functionality, thereby reducing file size and enhancing rendering efficiency; and
    executing the minified one or more interface graphic module templates to format display structures, minimizing required scrolling for the computer interface and reducing processing overhead via the data display control module.

8. The processor-based method of claim 7, wherein generating the optimized computer interface via the display control module comprises utilizing only the regimen data that meets or exceeds the confidence factor.

9. The processor-based method of claim 7, wherein calculating proportions of the itemsets comprises utilizing a hierarchical tree structure for the first data and second data itemsets.

10. The processor-based method of claim 7, wherein the first data itemsets comprise information relating to a specific vaccination being administered, a first type/route, trade names of vaccinations, and administrative data relating to the first regimen.

11. The processor-based method of claim 10, wherein the second itemsets comprises data relating to at least two of specific patients and related socioeconomic, environmental, biomedical factors, genetic factors, individual health status and health behaviors, biomedical and genetic factors, and at least one of resource use, outcomes, financing, and expenditures.

12. The processor-based method of claim 7, wherein generating the optimized computer interface comprises utilizing interface graphics module templates that are based on the confidence factor for a least some of the calculated proportions.

13. A system for generating an optimized computer interface for a regimen, comprising:
 a processing apparatus;
 a memory operatively coupled to the processing apparatus, the memory configured to store a nested hierarchy of first data itemsets and second itemsets configured as an array data structure;
 an interface graphics module, comprising a plurality of interface graphics module templates configured to format one or more display structures; and
 a data display control module;
 wherein the processing apparatus is configured to
  associate first data itemsets and second itemsets with one or more rules comprising a plurality of rule portions for executing the regimen;
  apply a first constraint utilizing proportions of the itemsets for the regimen;
  apply a second constraint utilizing a confidence factor, wherein the confidence factor represents an estimate of the probability of a rule portion being associated with another rule portion, thereby reflecting the statistical relevance of the data;
  selecting one or more of the interface graphic module templates based on the applied first constraint and second constraint, wherein the selecting is based on one or more the proportions meeting or exceeding the confidence factor;
  perform minification on the selected one or more interface graphic module templates, wherein the minification optimizes display data by removing extraneous code elements that do not affect functionality, thereby reducing file size and enhancing rendering efficiency; and
  execute the minified one or more interface graphic module templates to format display structures, minimizing required scrolling for the computer interface and reducing processing overhead via the data display control module.

14. The system of claim 13, wherein the processing apparatus is configured to calculate proportions of the itemsets utilizing a hierarchical tree structure for the first data and second data itemsets.

15. The system of claim 13, wherein the first data itemsets comprise information relating to a specific vaccination being administered, a first type/route, trade names of vaccinations, and administrative data relating to the regimen.

16. The system of claim 15, wherein the second data itemsets comprises data relating to at least two of specific patients and related socioeconomic, environmental, biomedical factors, genetic factors, individual health status and health behaviors, biomedical and genetic factors, and at least one of resource use, outcomes, financing, and expenditures.

17. The system of claim 13, wherein the regimen data comprises flags for data indicating a borderline or out-of-bounds condition for the first data.

* * * * *